(12) United States Patent
Romo, III

(10) Patent No.: US 6,454,803 B1
(45) Date of Patent: Sep. 24, 2002

(54) EXTERNAL NASAL VALVE BATTEN IMPLANT DEVICE AND METHOD

(76) Inventor: Thomas Romo, III, 150 Broadway, Suite 616, New York, NY (US) 10038

( * ) Notice: Subject to any disclaimer, the term of this patent is extended or adjusted under 35 U.S.C. 154(b) by 0 days.

(21) Appl. No.: 09/576,513

(22) Filed: May 23, 2000

(51) Int. Cl.$^7$ .................................................. A61F 2/18
(52) U.S. Cl. ....................................................... 623/10
(58) Field of Search ............................... 623/10, 11.11, 623/14.12, 23.72

(56) References Cited

U.S. PATENT DOCUMENTS

| | | |
|---|---|---|
| 4,938,234 A | 7/1990 | Capriotti |
| 4,994,084 A | 2/1991 | Brennan |
| 5,030,232 A | 7/1991 | Pham |
| 5,041,138 A | 8/1991 | Vacanti |
| 5,053,050 A | 10/1991 | Itay |
| 5,098,779 A * | 3/1992 | Kranzler et al. ............. 623/11 |
| 5,112,353 A | 5/1992 | Johansson |
| 5,413,600 A * | 5/1995 | Mittelman .................... 623/10 |
| 5,786,217 A | 7/1998 | Tubo |
| 5,842,477 A | 12/1998 | Naughton |
| 5,876,435 A | 3/1999 | Swords |
| 5,916,557 A | 6/1999 | Berlowitz-Terrant |
| 6,001,352 A | 12/1999 | Boyan |

\* cited by examiner

*Primary Examiner*—David J. Isabella

(57) ABSTRACT

An implant utilized in nasal reconstructive surgeries. In the primary mode, the device is intended to provide support for the external nasal valve when natural cartilage is insufficient due to prior poorly-performed rhinoplasty, trauma, defects, or age. In this preferred mode, the device is an elongated, concave, oval-shaped member, preferably constructed of a porous polyethylene. A unique method of the implantation thereof is also provided, wherein the implant is placed through an external rhinoplasty approach. More particularly, residual lower lateral cartilage is removed, the implant is inserted into an external valve pocket formed by the same, staying in place due to soft tissue therearound, and the nasal tip is re-draped. In total, usage of the foregoing allows patients to experience significant improvement in breathing and airway management following the external nasal valve reconstruction procedure.

4 Claims, 3 Drawing Sheets

EXTERNAL NASAL VALVE BATTEN IMPLANT DEVICE AND METHOD

BACKGROUND OF THE INVENTION

1. Field of the Invention

Figure 1:
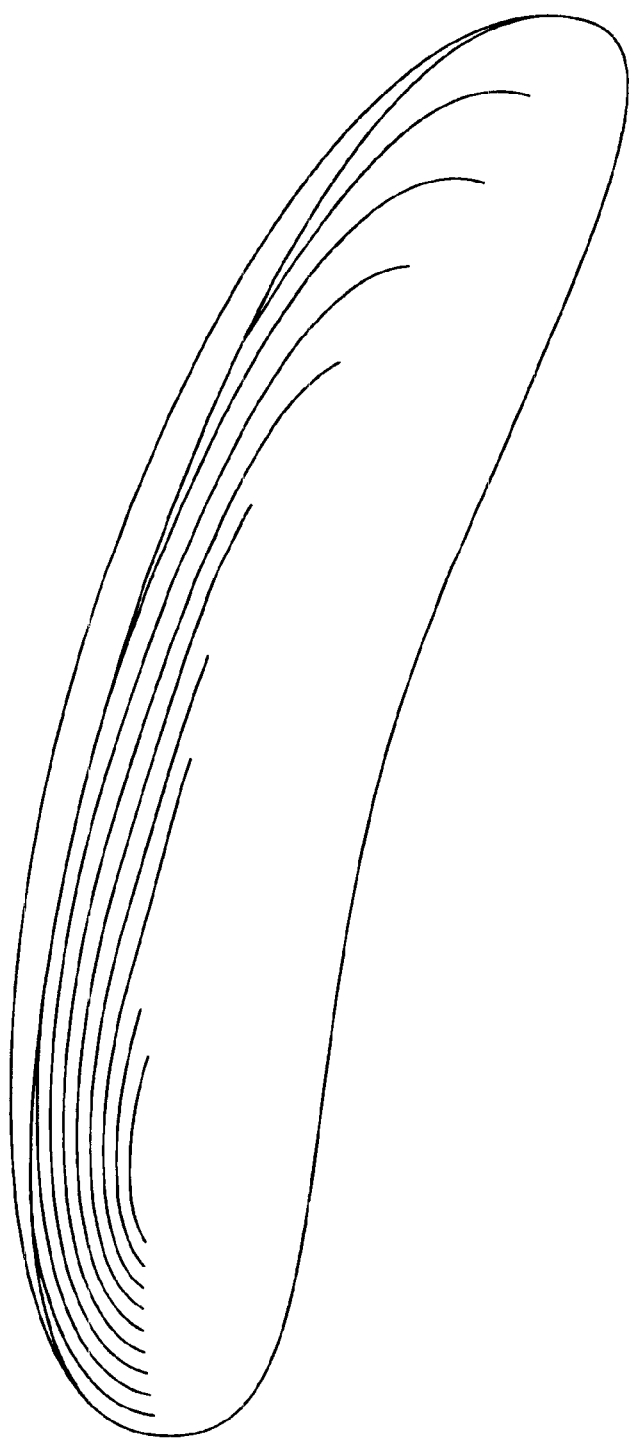

The present invention is an implant utilized in nasal reconstructive surgeries. In the primary mode, the device is intended to provide support for the external nasal valve when natural cartilage is insufficient due to prior poorly-performed rhinoplasty, trauma, defects, or age. In this preferred mode, the device is an elongated, concave, oval-shaped member, preferably constructed of a porous polyethylene. A unique method of the implantation thereof is also provided, wherein the implant is placed through an external rhinoplasty approach. More particularly, residual lower lateral cartilage is removed, the implant is inserted into an external valve pocket formed by the same, staying in place due to soft tissue therearound, and the nasal tip is re-draped. In total, usage of the foregoing allows patients to experience significant improvement in breathing and airway management following the external nasal valve reconstruction procedure.

2. Description of the Prior Art

Many innovations for nasal implants and polyethylene devices are provided in the prior art, described as follows. Although these inventions are suitable for the purposes they address, they differ from the present invention as contrasted herein. Following is a summary of patents most relevant to the invention at hand, including description of differences between features of the invention and those of the prior art.

1. U.S. Pat. No. 4,938,234, Invented by Capriotti, Entitled "Method Of Surgically Implanting A Contour Nasal Implant"

In the patent to Capriotti, a method is disclosed for surgically implanting a contour nasal implant into a nose of a patient to elevate the nasal tip and to augment and to improve the frontal and profile views of the patient's nose. The method comprises the steps of drawing, onto the nose of a patient into which a contour nasal implant is to be surgically implanted, a line connecting the highest points of the superior palpebral sulci such that the line crosses the nasal dorsum at a point representing the nasion and the highest point of implant insertion; placing two pledgets in each nostril in the nose of the patient; performing an open rhinoplasty incision into the skin located between the nostrils of the patient; retracting superiorly the columella skin off of the lower lateral cartilages on each side of the nostril up to the highest point of the natural dome of the nose of the patient; dissecting the skin off of the dorsum of the nose to the line previously drawn across the nasal dorsum; inserting a contour nasal implant having an elongated central member having a dorsal section, a predetermined shaped tip and a keel having a selected width and length which is located under the predetermined shaped tip with the keel thereof extending downward between the lower lateral cartilage until the desired implantation position is obtained; and suturing the rhinoplasty incision in the skin between the nostrils.

2. U.S. Pat. No. 5,030,232, Invented by Pham, Entitled "Nasal Implant Device With Improved Contour"

The nasal implant of the Pham invention is characterized by a composition of hard-grade silicone fashioned into a special shape. One variation in the composition material is to use soft silicone only for the tip in order to overcome the fear of some surgeons to use hard silicone in this particular area. A special and improved shape of the implant, in the form of a modified hourglass, provides a well rounded and larger tip portion thanb that of the prior art. The supra-tip of this improved implant shows a depression dorsally, is less wide than the rest of the implant and has a pronounced slope laterally. These features, particularly at the supra-tip region avoid the unnatural effects of the prior art devices. Moreover this implant has a variable thickness form upper end to tip—that is it starts thin, increases in thickness and then goes thinner again—whereas the prior art starts thin and continually increases throughout.

3. U.S. Pat. No. 5,112,353, Invented by Johansson et al., Entitled "Contour Nasal Implant"

In the patent to Johansson et al., a contour nasal implant adapted to be used in rhinoplasty surgery is shown. The contour nasal implant includes an elongated, central member having a first end and a second end wherein the second end is spaced a predetermined distance from the first end. The first end of the elongated central member is flared to define a dorsal support end or dorsal section which is adapted to be positioned over the nasal dorsum in the nose of a patient to augment the frontal and profile views of the nose along the nasal dorsum. The second end includes a tip having a predetermined shape which is located on the same side of the elongated central member as the dorsal support end. A second end includes a keel having a selected width and length and the keel is located on the second end under the predetermined shaped tip. The keel is positioned substantially perpendicular to the elongated central member and is positioned such that the length of the keel is generally parallel to the elongated central member. The tip is operative, when implanted into the nose of a patient, to reshape and elevate the nasal tip of the nose of a patient. The tip and the dorsal support end contour and shape the frontal and profile views of the nose of a patient.

4. U.S. Pat. No. 4,994,084, Invented by Brennan, Entitled "Reconstructive Surgery Method And Implant"

The Brennan invention describes a homograft implant made from prepackaged, processed homograft material. The homograft material is taken in its purchased dehydrated form and cut into strips of varying shapes and sized. The strips are then adhesively secured together in a laminar manner by a tissue adhesive to form the desired shape and density of the implant. Once the implant has been made, it may then be surgically implanted in a desired location, immediately beneath the patient's dermis so as to alter the exterior appearance of the patient at the implant site. Since the implant is formed of dehydrated homograft material, endogenous tissue readily attaches to the implant after a short period of time, so that the implant becomes integral with the body.

5. U.S. Pat. No. 5,876,435, Invented by Swords et al., Entitled "Coupling for Porous Resin Orbital Implant and Ocular Prosthesis"

In the patent to Swords et al. an improved coupling method and device for an ocular prosthesis to a porous polyethylene implant is provided. According to the invention, a small surgical screws having a domed head is inserted into a porous plastic implant after the implant has been implanted into an enucleated orbit allowed to vascularize. The domed head projects from the anterior surface of the implant which is covered by conjunctive tissue and is received by a complementary cavity on the rear surface of the ocular prosthesis.

6. U.S. Pat. No. 5,053,050, Invented Itay, Entitled "Compositions for Repair of Cartilage and Bone"

In the patent to Itay, a defect is provided in cartilage or bone, or both, to excize damaged or pathological tissue, and it is filled with an implant having capability for complete regeneration of the skeletal tissue as a chondrogenic or osteogenic phenotype. The implant comprises cells expressing a chondrocyte phenotype (80×10$^6$ cells/ml) embedded in a biocompatible matrix having about 20% serum, which provides a permissive environment for maturation and transformation of the implant to a fully integrated state with the surrounding tissue. A portion of the implant may comprise a bone segment or a bone substitute.

7. U.S. Pat. No. 5,786,217 Invented by Tubo et al., Entitled "Methods and Compositions for the Repair of Articular Cartilage Defects in Mammals"

Provided in the patent to Tubo et al. are methods and compositions for the repair of articular cartilage defects in a mammal. Denuded chondrogenic cells are proliferated ex vivo as monolayer cultures in order to expand the pool of available chondrogenic cells. During proliferation the chondrogenic cells stop secreting the extracellular matrix components, type II collagen and sulfated proteoglycans. The proliferated cells then are seeded into a pre-shaped well having a cell contacting, cell abhesive surface. The cells cultured in the well redifferentiate and begin to secrete cartilage-specific extracellular matrix again. Accordingly, essentially unlimited amounts of synthetic cartilage may be prepared from small samples of biopsy tissue. Also provided are methods for surgically repairing articular cartilage defects in mammals using the synthetic cartilage prepared in accordance with the invention.

8. U.S. Pat. No. 5,842,477, Invented by Naughton et al., Entitled "Method for Repairing Cartilage"

The Naughton et al. invention relates to methods of making and/or repairing cartilage in vivo comprising implanting into a patient, at a site of cartilage damage or loss, a biocompatible, non-living three-dimensional scaffold or framework structure in combination with periosteal/ perichondrial tissue that can be used to hold the scaffold in place and provides a source of chondrocyte progenitor cells, chondrocytes and other stromal cells for attachment to the scaffold in vivo. In addition, a preparation of cells that can include chondrocytes, chondrocyte progenitor cells or other stromal cells is administered, either before, during or after implantation of the scaffold and/or the periosteal perichondrial tissue; the cells are administered directly into the site of the implant in vivo and promote the induction of factors that enhance chondrogenesis and the migration of chondrocytes, progenitor cells and other stromal cells from the adjacent in vivo environment into the scaffold for the production of new cartilage at the site of implantation.

9. U.S. Pat. No. 5,916,557, Invented by Berlowitz-Terrant et al., Entitled "Methods Of Repairing Connective Tissues"

The Berlowitz-Terrant et al. invention relates to the use of an ECM-altering enzymatic activity, such as a proteoglycanase or a protease, to stimulate the generation of cartilage tissue by inducing chondrocytes to synthesize new cartilage matrix. It has been discovered that treating chondrocytes with an enzymatic activity that modifies the territorial ECM of the cell, especially cell surface proteoglycans, can in and of itself be sufficient to stimulate cartilage production by the chondrocytes. The subject invention can be employed therapeutically to correct or prevent degeneration of connective tissue. For instance, the present method can be used in the treatment of disorders comprising cartilage such as found in an diarthroidal joint (e.g. articular and interarticular cartilage), as well as in the treatment of tendon and ligamental tissues. Such disorders can range from chronic degeneration brought about by disease, overuse, or trauma, to plastic or reconstructive surgery. Moreover, the subject method may also be applied to both the development and implantation of prosthetic devices.

10. U.S. Pat. No. 5,041,138, Invented by Vacanti et al., Entitled "Neomorphogenesis Of Cartilage In vivo from Cell Culture"

The patent to Vacanti et al. describes methods and artificial matrices for the growth and implantation of cartilaginous structures and surfaces. In the preferred embodiments, chondrocytes are grown on biodegradable, biocompatible fibrous polymeric matrices. Optionally, the cells are proliferated in vitro until an adequate cell volume and density has developed for the cells to survive and proliferate in vivo. One advantage of the matrices is that they can be cast or molded into a desired shape, on an individual basis, so that the final product closely resembles a patient's own ear or nose. Alternatively, flexible matrices can be used which can be manipulated at the time of implantation, as in a joint, followed by remodeling through cell growth and proliferation in vivo. The cultured cells can also be maintained on the matrix in a nutrient media for production of bioactive molecules such as angiogenesis inhibiting factor.

11. U.S. Pat. No. 6,001,352, Invented by Boyan et al., Entitled "Resurfacing Cartilage Defects with Chrondrocytes Proliferated without Differentiation Using Platelet-Derived Growth Factor"

In the patent to Boyan et al., a method for stimulating chondrocyte proliferation and inhibiting chondrocyte differentiation along the endochondral developmental pathway is provided comprising contacting condrocytes with an effective amount of Platelet-Derived Growth Factor (PDGF) such as PDGF-BB, PDGF-AA OR PDGF-AB in the substantial absence of growth factors which promote cell differentiation. This allows such cells to be multiplied in culture for loading onto a scaffolding material and implanting into a cartilage or bone wound.

As outlined above, the prior art patents that relate to implants and nasal reconstructive surgeries largely entail elements such as: a nasal implant with composition of hard-grade silicone fashioned into a special shape with soft silicone used only for the tip; a homograft implant made from prepackaged and processed homograft material in dehydrated form and cut into strips of varying shapes and sizes; a porous polyethylene implant used in connection with an ocular prosthesis; a method for stimulating chondrocyte proliferation; methods where chondrocytes are grown on biodegradable fibrous polymeric matrices; and various other traditional implantation devices and methods.

In contrast to all of the above, the present invention is an elongated, concave, oval-shaped implant, constructed of a porous polyethylene, to be utilized in nasal reconstructive surgeries. A unique method allows for a convenient implantation means that has significant cosmetic benefits. In addition, usage of the foregoing allows for significant improvement in breathing and airway management following the external nasal valve reconstruction procedure.

SUMMARY OF THE INVENTION

As noted, the present invention is an implant utilized in nasal reconstructive surgeries, especially to provide support for the external nasal valve when cartilage is insufficient. In the preferred mode, the device is concave and oval-shaped, constructed of a porous polyethylene. Usage of the foregoing allows patients to experience improvement in breathing and airway management in addition to an improved appearance.

Thus, the implant of the present invention is intended to repair compromised skin-soft tissue envelopes which are secondary to such things as congenital defects, prior rhinoplasty surgery, heavy smoking, cocaine abuse, or simple adverse effects of aging.

According to the foregoing, it is an object of the present invention to restore or improve the patient's respiratory function.

It is a further goal of the present invention to provide reestablishment of the desired aesthetic nasal contour.

As such, it is a specific object of the present invention to allow for fibrovascular ingrowth, which lends great stability to the implant.

It is a particular aim of the applicant to provide a structurally stable implantation device that does not shift, rotate, or otherwise change position following installation.

It is a goal of the applicant to provide a device that elicits minimal inflammation, and resists trauma and exposure.

Similarly, it is a goal of the applicant to provide an implant that is non-carcinogenic and antigenically inert.

It is an additional object of the invention to overcome the detriments related to cartilage used for optimal grafting material, such limited supply, time restraints, and morbidity associated with harvesting.

It is an additional object of the present invention to overcome the detriments related to synthetic materials with high infection and extrusion rates.

It is also an object of the present invention to allow for effective reconstruction while alleviating implant extrusion and skin erosion.

It is a goals of the invention to provide a device that may be used effectively in relatively thin-skinned areas, performing far better in said areas than silicone implants widely known in the art.

It is an object of the present invention to provide implants that may be easily removed postoperatively.

Further, it is an object of the invention and procedure to mitigate the level of swelling and recovery time associated with nasal reconstruction.

It is an object of the present invention to provide an implant which may be manufactured or configured in a number of shapes and sizes for the utmost in versatility.

It is an additional object of the present invention to provide an implant which may be used in conjunction with additional implants during the same procedure.

In total, the novel features considered characteristic for the invention are set forth in the claims. The invention itself both as to its construction and method of operation, will be best understood from the following description of the embodiments when read and understood in connection with the drawings provided.

DETAILED DESCRIPTION OF THE PREFERRED EMBODIMENT

The present invention is a nasal implant that is constructed of a porous polyethylene material. Importantly, the implant is pliable in nature, which enables the same to be sculpted by the surgeon or staff, resulting in the ideally sized article for implantation purposes.

Specifically, the soaking of the polyethylene implant in a substantially hot liquid, such as water or saline, increases the pliancy thereof. This functions to allow the implant to be bent, wherein the implant maintains the newly curved configuration following a cooling period. For the purposes of example, such configuration may be of an angle as illustrated in FIG. 1.

Slightly curved by the user to the angle most closely resembling natural or existing cartilage, then, the elongated, concave, oval-shaped implant is intended to simulate or replace cartilage for multiple beneficial purposes including restoring effective respiration and augmenting nasal form to provide an aesthetically pleasing appearance.

Perhaps the most significant aspect of the implant of the present invention is that the implant reacts favorably with surrounding host tissue. Specifically, the porous polyethylene utilized allows fibrovascular tissue ingrowth to fix the implant permanently, functioning to provide long-term structural support previously unavailable absent traditional grafting techniques.

In the preferred mode of manufacture and usage, the implant is manifested as an external nasal valve batten implant. In such an instance, the implant is used primarily to repair an incompetent nasal valve alleviating adverse effects of nasal obstruction and difficulty in breathing. In many instances, such implant is used to correct or otherwise mitigate the adverse effects of previous surgical procedures that were largely unsuccessful.

In other examples, the implant is used to correct or otherwise mitigate the adverse effects of trauma, be it through blunt force or burn damage. Finally, it should be noted that the implant of the present invention is quite suitable for usage to correct otherwise mitigate the adverse effects of a congenitally low dorsum.

Figure 2:
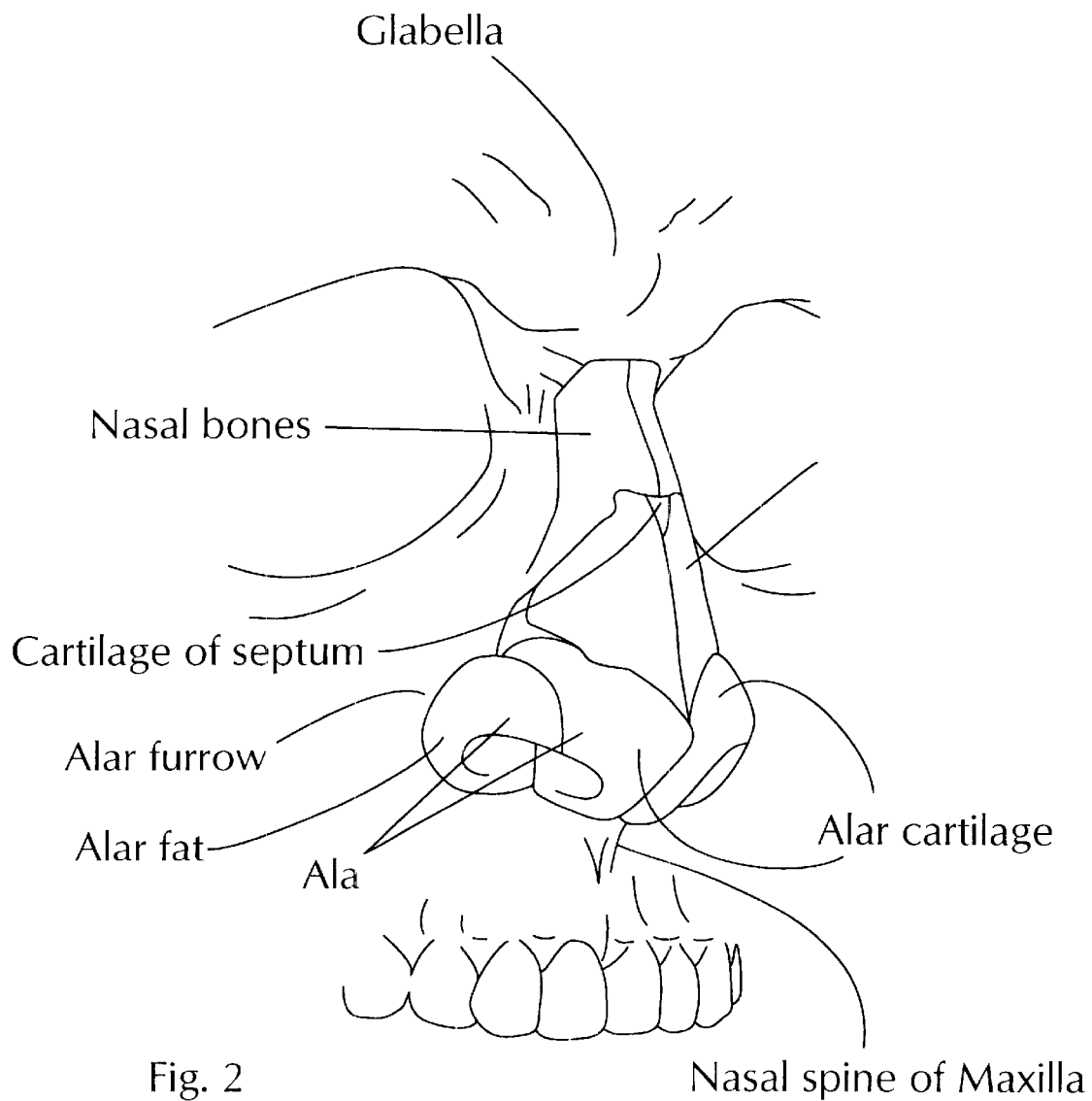
Figure 3:
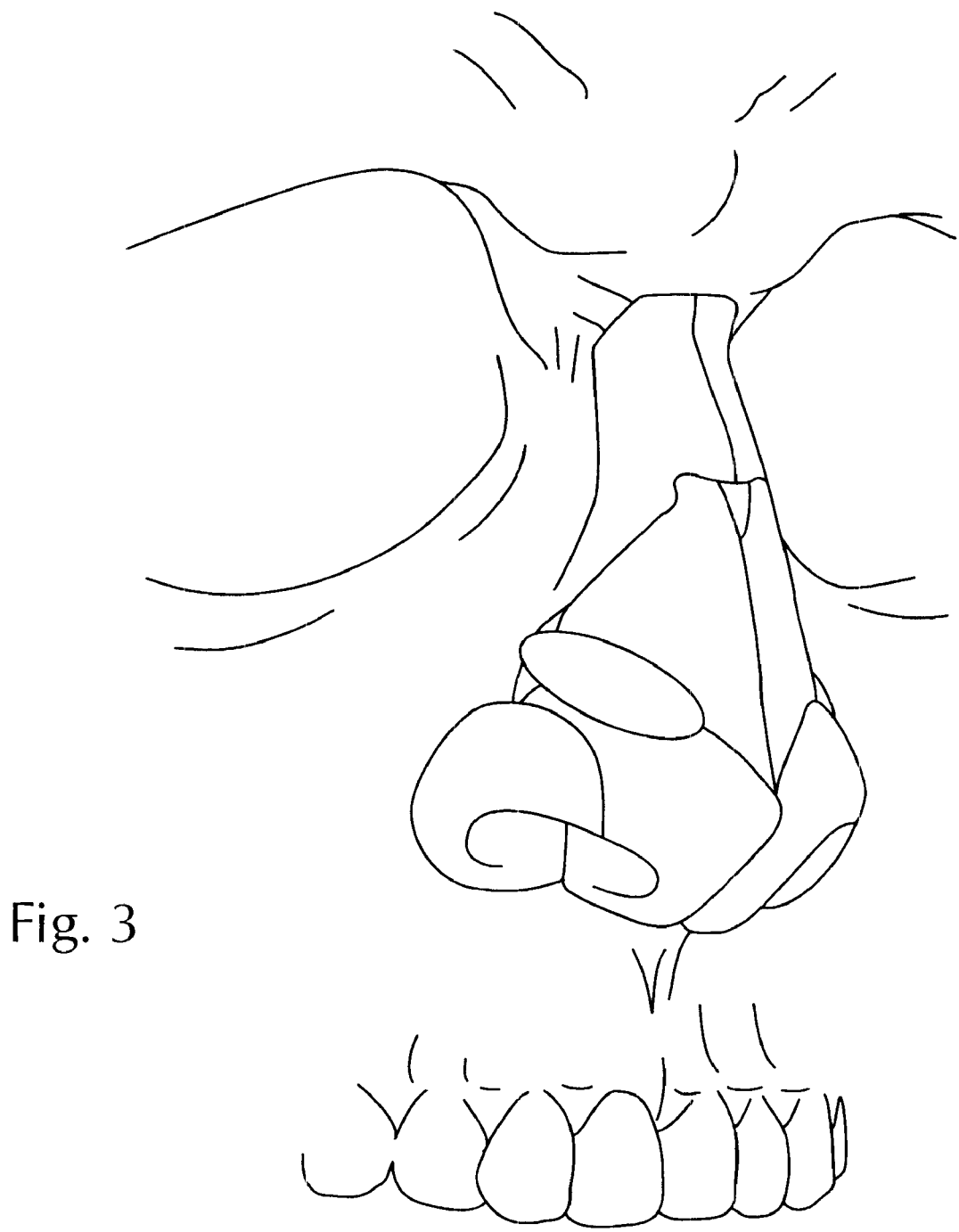

With regards to specific conditions that are effectively corrected by the implant of the present invention, FIG. 2 illustrates the relevant areas of the nose, prior to implantation, for the purpose of providing general context. The relevant areas include the Glabell (1), the Nasal bones (2), the Cartilage of septum (3), the Alar furrow (4), the Alar fat (5), the Alar cartilage (6) and the Nasal spine of Maxilla (7). FIG. 3, in turn, illustrates the implant of the present invention when fixed in place, according to one primary mode of usage thereof.

First, the implant is effectively used for augmentation of a platyrrhine nose, wherein the patient has previously experienced a substantially low, substantially wide dorsum, as well as poor tip projection and tip definition.

In addition, the implant is effectively used for augmentation of an overresected nose, wherein the patient has experienced a substantially narrowed dorsum and substantially narrowed, or pinched tip.

Moreover, the porous polyethylene strip may be very effectively utilized for augmentation of a saddle-type nose, wherein the patient has experienced substantially wide dorsum and loss of dorsal height.

In any such instance, the implant of the present invention may be usilized in the nasal tip to provide many benefits, including the increase of projection and definition of the nasal tip, as well as desired change of position of the nasal tip.

According to the foregoing, and evidencing the overall versatility of the porous polyethylene implant, the general configuration of the implant utilized may be selected from a group consisting of columella strut, plumper graft, premaxillary plumping implant, alar batten, dorsal tip implant. Although such represent the current primary configurations, other assemblies and forms of usage are certainly conceivable.

In the preferred mode of usage, the implant is manufactured in a general size of 25 mm×11 mm×0.85 mm. This size allows for placement of the implant anterior to a pyriform aperture, preferably 2–3 mm superior to a rim of the alar, and also 2–3 mm lateral to the nasal angle and tip. Such allows the same to effectively provide structural stability and a desired appearance, while still maintaining ease of implantation and modification or sculpting procedure.

It should also be noted that a plurality of the implants as described herein may be utilized in conjunction with one another in a related procedure. Such provides the surgeon considerable versatility in reconstruction where the patient has suffered severe congenital defects or trauma.

In general, as noted above, the implant may be easily and conveniently reduced in general size and configuration through usage of sculpting techniques. It is important to note that the porous polyethylene material is considerably easier to sculpt than grafted cartilage, enabling surgeons with less than perfect sculpting skills to effectively utilize the batten implant.

With regards to long-term effects of implantation of the porous polyethylene device, it is respectfully submitted that the same provides the greatest degree of long-term stability, absent the patient's own grafted cartilage when such is unavailable. Still, should the implant of the present invention need be removed for any purpose postoperatively, such may be performed conveniently and quickly, with little damage to the patient.

In general, the polyethylene implant is formed by the sintering of multiple particles together, functioning to form a general lattice-work configuration, within which pores are comprised. Thus, with further regard to the versatility afforded the surgeon when utilizing the porous polyethylene implant, a varying, or predetermined quantity of pores within the implant may be manufactured and utilized according to previously identified needs. Similarly, varying sizes of pores within the implant may be manufactured and utilized according to particular needs for particular procedures. Overall, in the preferred modes of utilization, the average porosity of the polyethylene implant is approximately 50%. Still, the porosity level can be greater or less, according to user preference and procedural requirements.

In many instances, the implant is configured as a 1.5 mm width sheet. Such size is often suitable for males requiring the reconstructive procedure. In other instances, the implant is configured as a 0.85 mm width sheet, effective for females requiring nasal reconstruction. In a third instance, the implant may be configured in a 0.5 mm width, should a thinner design be appropriate.

It is important to note that the color of the porous polyethylene implant closely resembles the color of host tissue located therearound. Such will clearly create an aesthetically pleasing appearance greatly desired by the patient. Moreover, the consistency of the implant closely resembles the consistency of host tissue located therearound. This results in a texture and feeling of the nose that most closely simulates actual, natural cartilage, much to the benefit of the patient as well.

According to the foregoing, the following is a summary of the method of implantation of the porous polyethylene, pliable nasal implant device. Patients selected for the nasal reconstruction procedure are evaluated according to the level to which nasal architectural support is lacking. Location of the support deficiency is determined and the optimal size and shape of the implant needed for augmentation is also determined.

The appropriate implant is then placed through an external rhinoplasty approach, wherein residual lower lateral cartilage is removed. The implant is then inserted into an external valve pocket formed therein and stays in place due to soft tissue therearound. Specifically, the implants are inserted into the appropriate pocket and secured to the lateral edge of the residual tip cartilage.

The nasal tip is subsequently re-draped therearound. This functions to restore respiration and functions to augment nasal form to provide an aesthetically pleasing appearance. The implant reacts favorably with surrounding host tissue, allowing fibrovascular tissue ingrowth to fix the implant permanently. Such functions to provide long-term structural support previously unattained through conventional methods.

While the invention has been described as embodied, it is not intended to be limited to the details shown, since it will be understood that various omissions, modifications, substitutions and changes in the forms and details of the device illustrated and in its operation can be made by those skilled in the art without departing in any way from the spirit of the invention.

Without further analysis, the foregoing will so fully reveal the gist of the present invention that others can readily adapt it for various applications without omitting features that, from the standpoint of prior art, constitute essential characteristics of the generic or specific aspects of this invention. What is claimed as new and desired to be protected by Letters Patent is set forth in the appended claims.

What is claimed is:

1. A nasal valve batten implant for reconstruction of an external rhinoplasty comprising an oval-shaped porous polyethylene device having a concave outer surface to simulate the curvature of the natural cartilage to be replaced;

the implant being sized and configured to be inserted into an external valve pocket formed by the removal of a lower lateral cartilage; and the implant being pliable and able to be sculpted to simulate the cartilage thereby restoring respiration wherein the porous implant allows fibrovascular tissue ingrowth to fix the implant in place to provide long term structural support.

2. A method for nasal reconstructive surgery comprising forming an external valve pocket by removing a lower lateral cartilage;

inserting an oval shaped porous polyethylene device having a concave outer surface to simulate the curvature of the natural cartilage to be replaced;

the implant being sized and configured to be inserted into an external valve pocket;

the implant being pliable and able to be sculpted to simulate the cartilage thereby restoring respiration; and redraping the nasal tip wherein the implant allows fibrovascular tissue ingrowth to fix the implant in place to provide long term structural support.

3. The device as described in claim 1, with the implant having a dimension of 25 mm×11 mm×0.85 mm.

4. The device as described in claim 1, wherein the average porosity according to the total volume of the implant is 50%.

* * * * *